(12) United States Patent
Calloura

(10) Patent No.: US 6,878,057 B1
(45) Date of Patent: Apr. 12, 2005

(54) SYSTEM FOR FILTERING AND SCENTING OF THE AIR OF INDIVIDUAL ROOMS OF A BUILDING

(76) Inventor: Derek S. Calloura, 115 Urbana Dr., Lafayette, LA (US) 70506

( * ) Notice: Subject to any disclaimer, the term of this patent is extended or adjusted under 35 U.S.C. 154(b) by 0 days.

(21) Appl. No.: 10/385,074

(22) Filed: Mar. 10, 2003

(51) Int. Cl.[7] .............................. A61L 9/00; F24F 13/28
(52) U.S. Cl. ...................... 454/299; 422/123; 454/291
(58) Field of Search ................... 454/289, 290, 454/291, 292, 299, 301, 309, 319, 320, 328; 422/123, 422/124

(56) References Cited

U.S. PATENT DOCUMENTS

| | | | | |
|---|---|---|---|---|
| 5,240,653 A | * | 8/1993 | Ramkissoon | 261/99 |
| 5,269,723 A | * | 12/1993 | Bender | 454/157 |
| 5,273,690 A | * | 12/1993 | McDowell | 261/107 |
| D346,856 S | * | 5/1994 | Kany | D23/368 |
| 5,460,787 A | * | 10/1995 | Colon | 422/123 |
| 5,478,505 A | * | 12/1995 | McElfresh et al. | 261/30 |
| 5,947,815 A | * | 9/1999 | Danforth | 454/289 |
| 6,190,607 B1 | * | 2/2001 | Farmer | 422/5 |

* cited by examiner

*Primary Examiner*—Harold Joyce
(74) *Attorney, Agent, or Firm*—Joseph L. Lemoine, Jr.

(57) ABSTRACT

A system for individualized filtering and scenting of the air of individual rooms of a building which is serviced by a ducted central forced air handling system. The system includes a conventional "tri-louvered" ceiling register and a filtering and scenting element designed to be inserted and removed from said register without the necessity of removing the register from attachment to the ceiling. The filtering and scenting element is a filtration media disposed between layers of supporting frame-work.

10 Claims, 2 Drawing Sheets

US 6,878,057 B1

SYSTEM FOR FILTERING AND SCENTING OF THE AIR OF INDIVIDUAL ROOMS OF A BUILDING

FIELD OF INVENTION

The invention disclosed and claimed herein relates to the general field of central air conditioning (heating and/or cooling) of habitable structures, principally residential buildings. More particularly the invention herein disclosed and claimed relates to filtration of and/or scenting of the air as it circulates about the air conditioning system of a building. With additional particularity, the invention herein disclosed and claimed relates to an article of manufacture for use in combination with "tri-louvered" ceiling registers of individual rooms, to filter and/or scent air immediately prior to the air entering into individual rooms of building structures, thereby providing for individualized filtration and/or scenting of the air of different rooms of the building. The invention disclosed and claimed herein is designed to be used in connection with "tri-louvered" ceiling registers of existing design, without modification of said registers, or the necessity of removing said registers to install, remove or otherwise periodically change the filtering and/or scenting elements of the invention.

BACKGROUND OF INVENTION

Forced conditioning (heating, cooling and/or adjustment of humidity) of air by a centrally disposed unit ("central air conditioning") of structures, particularly habitable buildings, is well known in developed countries. In general, in such systems, air is drawn, into a central unit, which unit incorporates various means to heat and/or cool air as it passes through said unit. After passing through the central unit, duct-works are typically used to distribute the air into individual rooms of the structure. As air enters the room from a duct it is typically passed through a louvered register to help direct it more or less uniformly, as the occupant of the room may desire, about the room or area thereof. As heated and/or cooled air enters into a room, the air already present therein is displaced and, typically, at least part of it returned, by duct-work or passage-ways in the building, to the central unit, where additional heating and/or cooling, as may be desired, may be accomplished. Typically circulation, for heating and/or cooling is controlled by thermostat and will continue until a desired temperature or humidity has been established.

In a typical air conditioning system air is filtered at the air intake of the central unit. At that location the air is also sometimes scented. Filtering and/or scenting of the air at that location does have advantages, including but not necessarily limited to: the entirety of the air can be filtered with filtering/scenting means; cleansing the air immediately before entry into the central unit helps maintain the cleanliness of, thus reduce maintenance of, the various elements of the central unit and duct-works thereafter; and/or, by design that area is made readily accessible, thereby cleaning or changing of the filter elements is relatively facile. However, filtering and/or scenting of the air at the intake to the main/central unit has certain disadvantages, including but not necessarily limited to: a filter at the intake of the main/central unit cannot remove dust, dirt and/or other contaminants that become entrained in the air during passage of the air through duct-work of the building and does not accommodate special filtering and/or scenting desires of the occupants of individual rooms. Moreover the heating and cooling elements of the central unit tend to remove or alter scent as scented air passes across them.

It would therefore, accordingly, be desirable to have a means to be provided where air can be at least supplementally filtered and/or scented immediately entering individual rooms of a building serviced by one or more central heating and/or air conditioning systems. To this end the invention herein disclosed is directed.

Prior art discloses certain attempts to filter air as it enters individual rooms of a building. Some of these attempts have focused on providing the air duct with some sort of filter holder. Other attempts have focused on providing the individual rooms with air registers which have been specially designed to receive an air filter. These designs focus on providing modified apparatus for receiving a filter, and such apparatus must be removed or loosened to install, remove or otherwise periodically change the air filters thereof, and, the filters of these designs are not specially adapted to disperse scenting agents into the air. Whereas the invention disclosed and claimed herein is specially adapted to both filter air and impart a scent thereto, as it enters individual rooms of a building structure, and is designed to be used in conjunction with existing "tri-louvered" ceiling registers, without modification thereof, and without the necessity of removing or loosening such registers to install said article of manufacture.

OBJECTS OF THE INVENTION

A general object of the invention disclosed and claimed is to provide a system for filtration and/or scenting of air, which is circulating in a central air conditioning system, immediately prior to dispersal of the air into the individual rooms of a building serviced by such system. Another object of the invention is to provide a system, for filtration and scenting of air immediately prior to dispersal into individual rooms of a building serviced by central air conditioning which is adapted for us in existing ceiling registers of "tri-louvered" design. Yet another object of the invention is to provide said system with a filter/scenting element which may be facilely installed in an operative position, removed therefrom, and periodically changed, without modification, removal or loosening of fastened together elements of said system. Yet another object of the invention is to provide a scenting element capable of dispersing scent to air over an extended length of time.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

Figure 1:
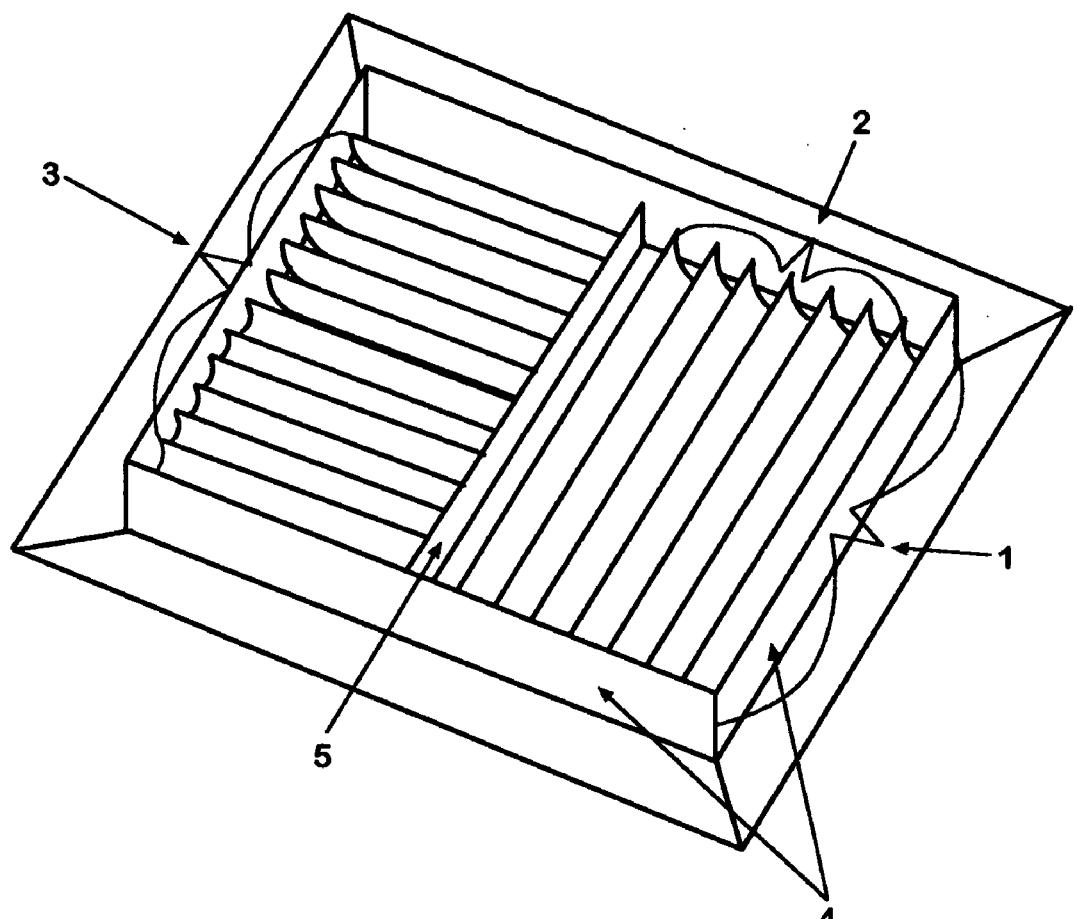
FIG. 1 is a perspective view of the top (facing duct-work) side of a "tri-louvered" ceiling register of existing design.

In the field of central heating and/or cooling of air of habitable buildings, in particular residential structures, called "tri-louvered" ceiling registers, such as illustrated in FIG. 1, are in widespread use. They are designed to be horizontally disposed over the opening of duct-work through which air, circulating about the building enters individual rooms of the building through the ceilings thereof. Depending on the size of an individual room it may have one or more such registers. As illustrated in FIG. 1, such registers are generally of square shape and have three sets of louvers, each of which set includes a plurality of spaced apart blades pivotal about a horizontal axis near the top of each blade. Typically one set of louvers 2 will run the full length of the opening 1 of register. Typically the other two sets of louvers 3 will be disposed perpendicularly to said first set of louvers 2 and run approximately half of the width of the opening of the register. By adjusting the angle of the blades of said louvers variable amounts of air can be directed into the room serviced thereby in different directions.

On the top of tri-louvered ceiling registers (which is typically disposed within the duct-work when the register is operatively installed) there is typically a square, box-like structure having vertical sides 4. Typically said box-like structure has a vertical partition 5 approximately mid-way. The upper edges of blades 2 and 3 of the register are typically pivotally disposed to said vertical sides 4 and partition 5. Accordingly the upper edges of the spaced apart blades of louvers 2 and 3 effectively form a "grated floor" (having spaces between horizontal elements thereof) of said box-like structure. The invention disclosed and claimed herein is adapted for use in conjunction with ceiling registers of this design. In operative position, the filtration/scenting element of the invention herein disclosed and claimed is designed to rest upon said grated floor of said box-like structure. It is designed to be positioned therein and removed therefrom through a space between blades 2 of the louver (or between one of said blades 2 and adjacent vertical side 4, without the necessity of removing or loosening the register from position).

Figure 3:
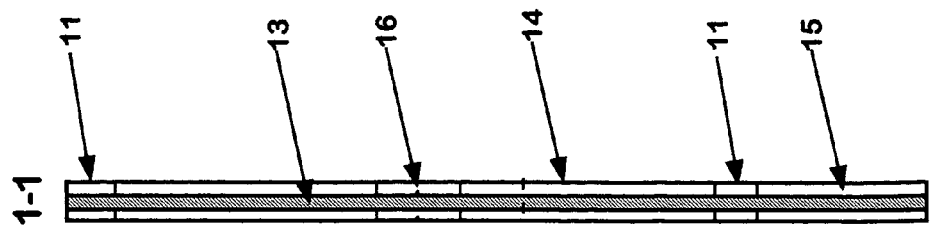
FIG. 3 is a sectional view of the embodiment of the invention of FIG. 2 along line 1—1.
Figure 2:
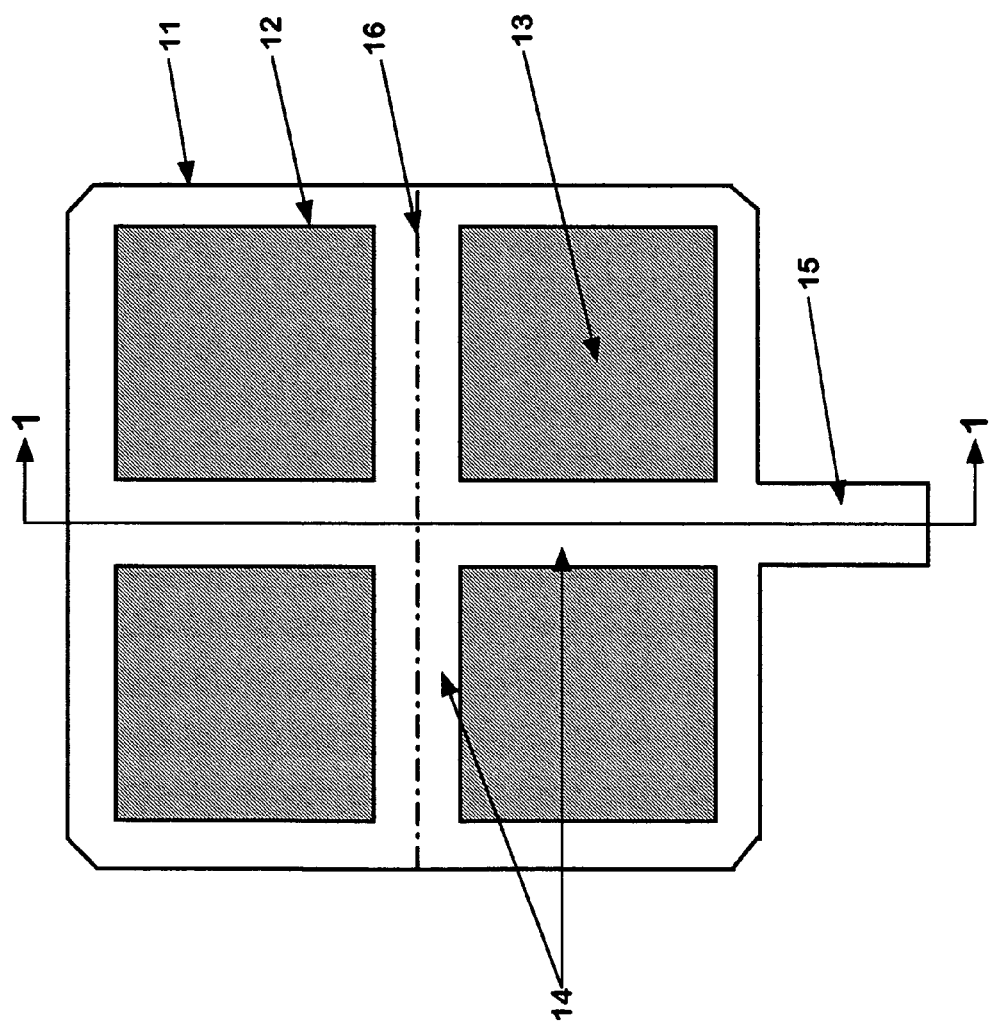
FIG. 2 is a top plan view of the preferred embodiment of the filter/scenting element of the invention disclosed and claimed herein.

The preferred embodiment of the filtration/scenting element of the invention is shown in FIGS. 2 and 3. As is shown therein said preferred embodiment may be generally characterized as a generally sheet-like article. Said sheet-like article has a length, a width and a thickness. The length and width of the filtration/scenting element will be determined by the size of the box-like structure defined by vertical sides 4 of the tri-louvered ceiling register (FIG. 1). A length and width of said filtration/scenting element will be chosen which substantially covers the area defined by said box-like structure, but does not fit against the vertical sides 4 so tightly that said element is difficult to install by sliding through long blades 2 of the louver or a long blade of louver 2 and the end of opening 1. The thickness of the filtration/scenting element will be determined by the space between long blades 2 of the register (or the space between the long blade thereof which is nearest to the end of opening 1 and adjacent vertical side 4). Typically both spaces are about the same and are approximately ½ of an inch.

The thickness of the filtration/scenting element must be sufficiently thin to easily slide through said space. It will be appreciated by those skilled in the art that the space between said long blades 2, or the long blade 2 which is adjacent to the end of opening 1 may vary, depending on the angle said blades may be set, and if said blades are "closed" there may be little or no space therebetween. This is not how the invention herein disclosed and claimed is to be understood. Rather it should be understood that since said blades are pivotally disposed, they may be pivoted to the open position in order to install or remove the filtration/scenting element of the invention. Thereafter, the blades of the louver may be returned to their original position if desired. In practice, however, the filtration/scenting element is mad as thin as practical, to at least reduce the necessity, in most cases, of having to adjust the blades of the register to install or remove said element from operative position within the tri-louvered ceiling register.

The filtration/scenting element of the invention includes frame 11, air passages 12, filter media 13, and may include cross-members 14 and extended tab 15.

In the preferred embodiment of the invention the material of frame 11 should be sufficiently rigid so as to be supportive of its own weight when held horizontally by one edge thereof. As the filtration/scenting element of the invention is intended to be frequently replaced and the used element disposed, materials which are readily biodegradable are preferred. To this end heavy-weight papers ("cardboards") and the like are preferred.

In the preferred embodiment frame 11 will be comprised of at least two parallel layers of material having at least one layer of filter material 13 which is disposed at least partially between said layers and extending over air passages 12. Filter material 13 may be a fibrous filter material, such as glass, cellulose, polyester, cotton or other fibers suitable for use as air filtration media, or various open-cell foam materials also commonly used to filter air. Said filter material, disposed between layers of frame 11, will contain a plurality of void spaces ("cells") which may be used as "reservoirs" for chemical scenting agents. The distance between the layers of frame 11, the size of air passages 12, and the material of the filter media 13 may all be varied so as to enlarge or reduce number and size of said cells, and thereby vary the effective longevity and potency of scenting that the article of manufacture is capable of. In addition thereto, the material of the frame 11 may also be varied to vary the scenting effect of the invention. Namely, if the material of frame 11, or a coating thereof, makes it more impervious to scenting agents, then the invention has a tendency to release scent over a longer period of time, but with less potency over that length of time. On the other hand if the material of frame 11 is highly porous then the scent will be released more quickly therethrough, thus have more potency but a shorter longevity. Each of these factors may be varied, as well as the scenting agent itself, so as to obtain a desired longevity and potency of scenting.

The filtering/scenting element of the invention (shown in FIGS. 2 and 3) may also include one or more cross-members 14, which in the preferred embodiment of the invention will be composed of at least two layers of material with a layer of filter media 13 disposed therebetween. In the preferred embodiment cross-members 14 will integrally form with the material of frame 11. The width of said cross-members 14 may be varied so to increase or decrease (as may be desired) the available number of cells which are available for use as reservoirs for chemical scenting agents. As illustrated in FIGS. 2 and 3, in the preferred embodiment of the invention two mutually perpendicular cross-members 14 are utilized. In said embodiment the cross-member which runs parallel to the edge of frame 11 from which tab 15 extends is perforated along line 16, so as to make the article of manufacture bendable along said line. The purpose of this feature is to permit the filtration/scenting element of the invention to better conform itself to the inside of the ceiling register upon which it rests (when the vertical partition 5 of said register is elevated a height above the upper edge of the blades of the louvers 2 and 3 thereof).

In the preferred embodiment of the invention the filtration/scenting element thereof includes tab 15, which extends perpendicular from the outside of one of the edges of frame 11. The purpose of tab 15 is to facilitate installation and removal of the article of manufacture from a tri-louvered ceiling register, without the necessity of removing or loosening such register from its operative position over the opening of a room duct. Tab 15 is intended to be left protruding through the blades of the register. By grasping tab 15 the article of manufacture is easily pulled from operative position.

The invention is simple and easy to use. It may be used with or without use of a chemical scenting agent, as may be desired by the user. The filtration/scenting element of the invention is easily installed from below, into a tri-louvered ceiling register, by inserting it through the space between the long blade of louver 2 which is proximate to the end of the opening 1 of the register and said end of said register. Upon complete insertion through said space (except for tab 15, which is intentionally left out) the article of manufacture is designed to rest in place on the upper edges of louvers 2 and 3 and vertical partition 5 of the tri-louvered register. There both gravity and air flowing downward maintain the filtration/scenting element in place. When removal of the article of manufacture is desired (typically when the scent is exhausted or the filter media 13 is loaded up, which can be detected by decrease in air flowing from the register), it can easily be removed from the ceiling register by grasping tab 15 and pulling the article through the same space it was installed in.

It is thus to be appreciated that the principles and teachings of the present inventive disclosure constitute an advancement in the art. While the above description contains certain specificities, these should not be construed as limitations on the scope of the invention, but rather only as an exemplification of the preferred embodiments thereof. Accordingly, the scope of the present invention should be determined not only by the embodiments illustrated, but by the appended claims and their legal equivalents.

What is claimed is:

1. A system for filtering and scenting the air of an individual room of a building serviced by a forced air central unit, comprising:
    a. air transmissible port disposed on the ceiling of said individual room;
    b. air passage-way connecting the forced air from said central unit to said individual room of said building;
    c. tri-louvered ceiling register disposed on said ceiling over said air transmissible port, wherein the upper side of said register presents four vertically disposed sides defining an area therebetween and a bottom comprised of a plurality of pivotally disposed blades, the longitudes of a portion of said plurality of blades are disposed parallel to each other and parallel to at least one of said vertically disposed sides and are spaced apart from each other and from the vertically disposed side which they are parallel to; and,
    d. filtration and scenting element having a length, a width and a thickness, said length and width being sized to substantially cover said area between said vertically disposed sides of said tri-louvered register when horizontally disposed on the bottom thereof and said thickness being sized to slidably fit through the space between the blade of said tri-louvered ceiling register which is nearest a vertically disposed side of said tri-louvered register which is parallel to said blade when said blade is pivoted to a position which maximizes the space therebetween.

2. The system of claim 1, wherein the filtration and scenting element is comprised of an outer frame and an air passageway therethrough, wherein said outer frame is comprised of two layers of parallel disposed material, and has a sheet of filtering medium disposed therebetween and extending across said air passageway.

3. The system of claim 2 wherein the upper and lower layers of said filtration and scenting element are comprised of a material which is sufficiently rigid such that when all three layers of material are assembled together said filtration and scenting element is supportive of its own weight when disposed horizontally by one edge thereof.

4. The system of claim 2 wherein said filter medium is comprised of glass fibers.

5. The system of claim 2 wherein said filter medium is comprised of cellulose fibers.

6. The system of claim 2 wherein said filter medium is comprised of polyester fibers.

7. The system of claim 2 wherein said filter medium is comprised of cotton fibers.

8. The system of claim 2 wherein said filter medium is comprised of an open cell expanded foam.

9. The system of claim 3 wherein said upper and lower layers are composed of heavy weight paper.

10. The system of claim 3 wherein said upper and lower layers are composed of cardboard.

* * * * *